US012629157B2

(12) United States Patent
Knopf

(10) Patent No.: US 12,629,157 B2
(45) Date of Patent: May 19, 2026

(54) SURGICAL SYSTEMS AND METHODS FOR POSITIONING OBJECTS USING AUGMENTED REALITY NAVIGATION

(71) Applicant: ARTHREX, INC., Naples, FL (US)

(72) Inventor: Jonathan Knopf, Naples, FL (US)

(73) Assignee: ARTHREX, INC., Naples, FL (US)

( * ) Notice: Subject to any disclaimer, the term of this patent is extended or adjusted under 35 U.S.C. 154(b) by 531 days.

(21) Appl. No.: 17/940,346

(22) Filed: Sep. 8, 2022

(65) Prior Publication Data

US 2023/0074630 A1 Mar. 9, 2023

Related U.S. Application Data

(60) Provisional application No. 63/241,758, filed on Sep. 8, 2021.

(51) Int. Cl.
*A61B 17/17* (2006.01)
*A61B 34/10* (2016.01)
(Continued)

(52) U.S. Cl.
CPC .......... *A61B 17/1703* (2013.01); *A61B 34/10* (2016.02); *A61B 34/20* (2016.02);
(Continued)

(58) Field of Classification Search
None
See application file for complete search history.

(56) References Cited

U.S. PATENT DOCUMENTS

2003/0233098 A1\* 12/2003 Markworth ............ A61B 17/17
606/96
2009/0088763 A1\* 4/2009 Aram ................... A61B 17/157
606/88
(Continued)

FOREIGN PATENT DOCUMENTS

WO 2014200017 A1 12/2014
WO 2018063528 A1 4/2018
WO 2018203304 A1 11/2018

OTHER PUBLICATIONS

Gu, Feasibility of Image-based Augmented Reality Guidance of Total Shoulder Arthroplasty Using Microsoft HoloLens 1, 15 pages, compiled Aug. 26, 2020.

(Continued)

*Primary Examiner* — Kent W Chang
*Assistant Examiner* — Jonathan M Cofino
(74) *Attorney, Agent, or Firm* — Carlson, Gaskey & Olds, P.C.

(57) ABSTRACT

Surgical systems and methods are provided that utilize augmented reality navigation and visualization techniques for transferring aspects of a preoperative surgical plan to an actual surgical site. The surgical systems and methods may be utilized to achieve accurate alignment of a surgical positioning object, such as a guide pin for guiding surgical reaming procedures, between the preoperative surgical plan and the intraoperative anatomy associated with the actual surgical site. Augmented reality may be utilized to achieve visualization of both an entry point and a drilling trajectory of the surgical positioning object in a manner that avoids occluding the intraoperative anatomy during the procedure.

22 Claims, 9 Drawing Sheets

(51) Int. Cl.

| | | |
|---|---|---|
| *A61B 34/20* | (2016.01) | |
| *A61B 90/00* | (2016.01) | |
| *G06T 19/00* | (2011.01) | |

(52) U.S. Cl.
    CPC ...... *G06T 19/006* (2013.01); *A61B 2034/105* (2016.02); *A61B 2034/107* (2016.02); *A61B 2034/2068* (2016.02); *A61B 2090/365* (2016.02)

(56) References Cited

U.S. PATENT DOCUMENTS

| | | | |
|---|---|---|---|
| 2018/0071032 A1* | 3/2018 | de Almeida Barreto ..................... G06T 19/006 | |
| 2018/0185100 A1* | 7/2018 | Weinstein ............... A61F 2/461 | |
| 2019/0380792 A1 | 12/2019 | Poltaretskyi et al. | |
| 2020/0082389 A1 | 3/2020 | Regev | |
| 2020/0085511 A1 | 3/2020 | Oezbek et al. | |
| 2020/0159313 A1 | 5/2020 | Gibby et al. | |
| 2020/0315711 A1* | 10/2020 | Richter .................. A61B 34/20 | |

| | | | |
|---|---|---|---|
| 2021/0093329 A1* | 4/2021 | Poltaretskyi ........... G16H 30/20 | |
| 2021/0093415 A1* | 4/2021 | Moore ..................... G06F 30/20 | |
| 2021/0161612 A1* | 6/2021 | Black ...................... G06F 3/011 | |
| 2021/0290319 A1* | 9/2021 | Poltaretskyi .............. G06T 7/55 | |
| 2021/0330402 A1* | 10/2021 | Abiven ................ A61B 90/361 | |
| 2022/0211444 A1* | 7/2022 | Dassonville ........... A61B 34/20 | |
| 2023/0060889 A1* | 3/2023 | Dacosta .............. A61B 17/152 | |

OTHER PUBLICATIONS

Schutz, Usability of Graphical Visualizations on a Tool-Mounted Interface for Spine Surgery, 17 pages, Journal of Imaging, 7, 159, Published Aug. 21, 2021.

International Search Report and Written Opinion of the International Searching Authority for International application No. PCT/US2022/042857 dated Dec. 16, 2022.

International Preliminary Report on Patentability for International application No. PCT/US2022/042857 dated Mar. 21, 2024.

Japanese Application No. 2024-515100, Notice of Reasons for Rejection, dated Jan. 16, 2025.

* cited by examiner

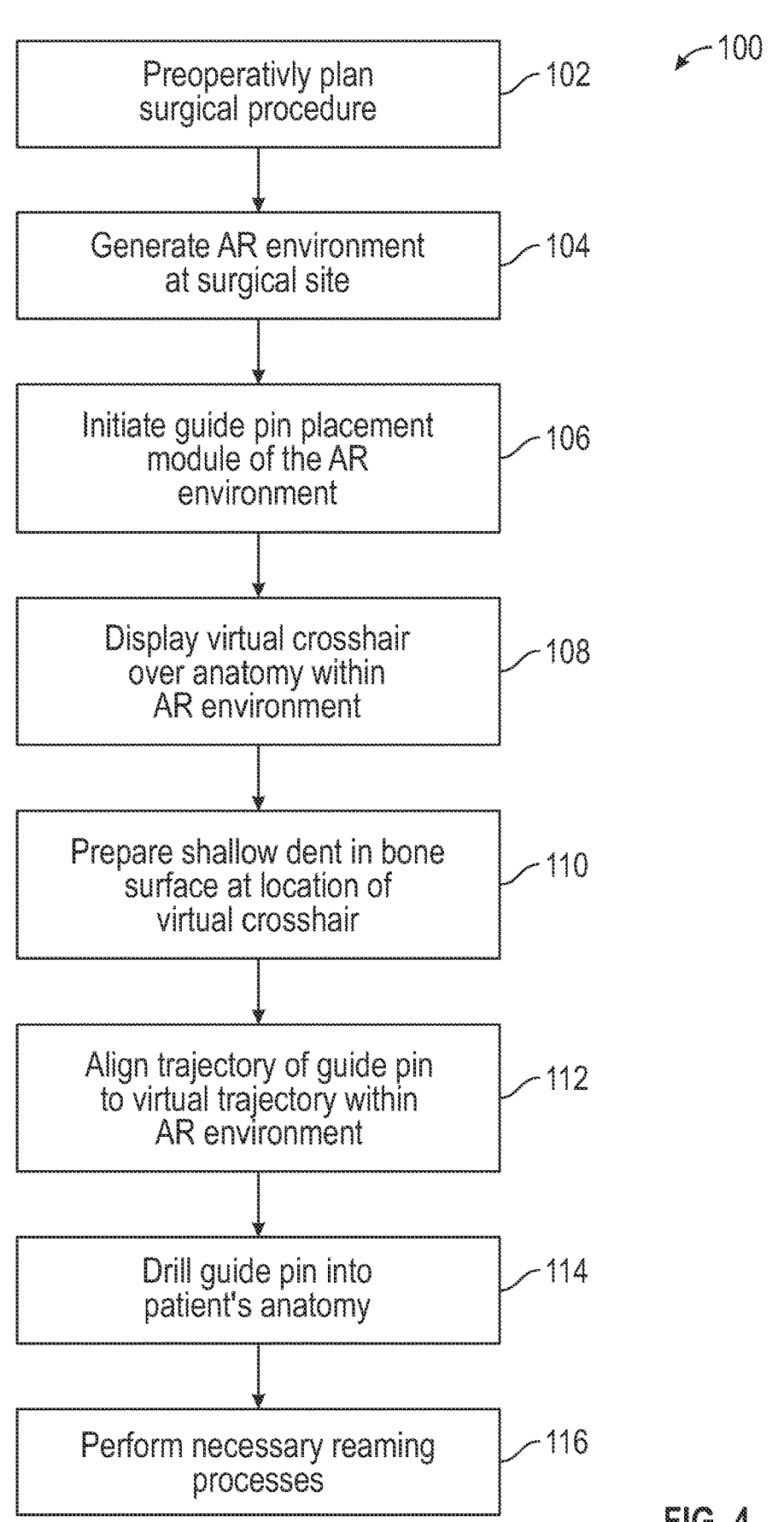

100

Preoperativly plan
surgical procedure — 102

Generate AR environment
at surgical site — 104

Initiate guide pin placement
module of the AR
environment — 106

Display virtual crosshair
over anatomy within
AR environment — 108

Prepare shallow dent in bone
surface at location of
virtual crosshair — 110

Align trajectory of guide pin
to virtual trajectory within
AR environment — 112

Drill guide pin into
patient's anatomy — 114

Perform necessary reaming
processes — 116

FIG. 4

SURGICAL SYSTEMS AND METHODS FOR POSITIONING OBJECTS USING AUGMENTED REALITY NAVIGATION

CROSS-REFERENCE TO RELATED APPLICATION

This disclosure claims priority to U.S. Provisional Application No. 63/241,758, which was filed on Sep. 8, 2021 and is incorporated herein by reference in its entirety.

BACKGROUND

This disclosure relates to the field of surgery, and more particularly to orthopedic surgical systems and methods for intraoperatively positioning objects, such as surgical guide pins, for example, by utilizing augmented reality navigation and visualization techniques.

Arthroplasty is a type of orthopedic surgical procedure performed to repair or replace diseased joints. Surgeons may desire to establish a preoperative surgical plan relating to preparation of a surgical site, selection of an implant, and placement of the implant at the surgical site prior to performing the arthroplasty.

In some techniques, a surgeon may utilize a guide pin to guide reaming of a bone surface for positioning the arthroplasty implant at the surgical site. Surgeons may desire improved intraoperative guidance for transferring aspects of the preoperative surgical plan to the surgical site in order to improve surgical outcomes.

SUMMARY

This disclosure relates to surgical systems and methods that utilize augmented reality navigation and visualization techniques for transferring aspects of a preoperative surgical plan to an actual surgical site.

An exemplary augmented reality system for a surgical system may include, inter alia, an augmented reality visualization device and a processor. The processor may be programmed to control the augmented reality visualization device to provide an augmented reality environment relative to a patient's anatomy. The processor may be further programmed to allow a user to interface with the augmented reality environment for intraoperatively achieving a desired entry point and a desired trajectory of a surgical positioning object relative to the patient's anatomy.

An exemplary surgical method may include, inter alia, intraoperatively demarcating a desired entry point and a desired trajectory of a surgical positioning object within an augmented reality environment produced by an augmented reality system. A visual indication of an accuracy between an actual trajectory and the desired trajectory of the surgical positioning object may be provided within the augmented reality environment.

Another exemplary surgical method may include, inter alia, positioning a tip of a surgical guide pin at a location of a bone surface of an anatomy that is indicated by a virtual crosshair, preparing an indentation at the location, pivoting the surgical guide pin about a pivot point established by the indentation, and aligning an actual trajectory of the surgical guide pin to a virtual trajectory of the surgical guide pin within an augmented reality environment.

BRIEF DESCRIPTION OF THE DRAWINGS

FIG. 4 schematically illustrates an exemplary surgical method that can be preoperatively planned and intraoperatively performed using the orthopedic surgical system of FIG. 1.

DETAILED DESCRIPTION

Figure 1:
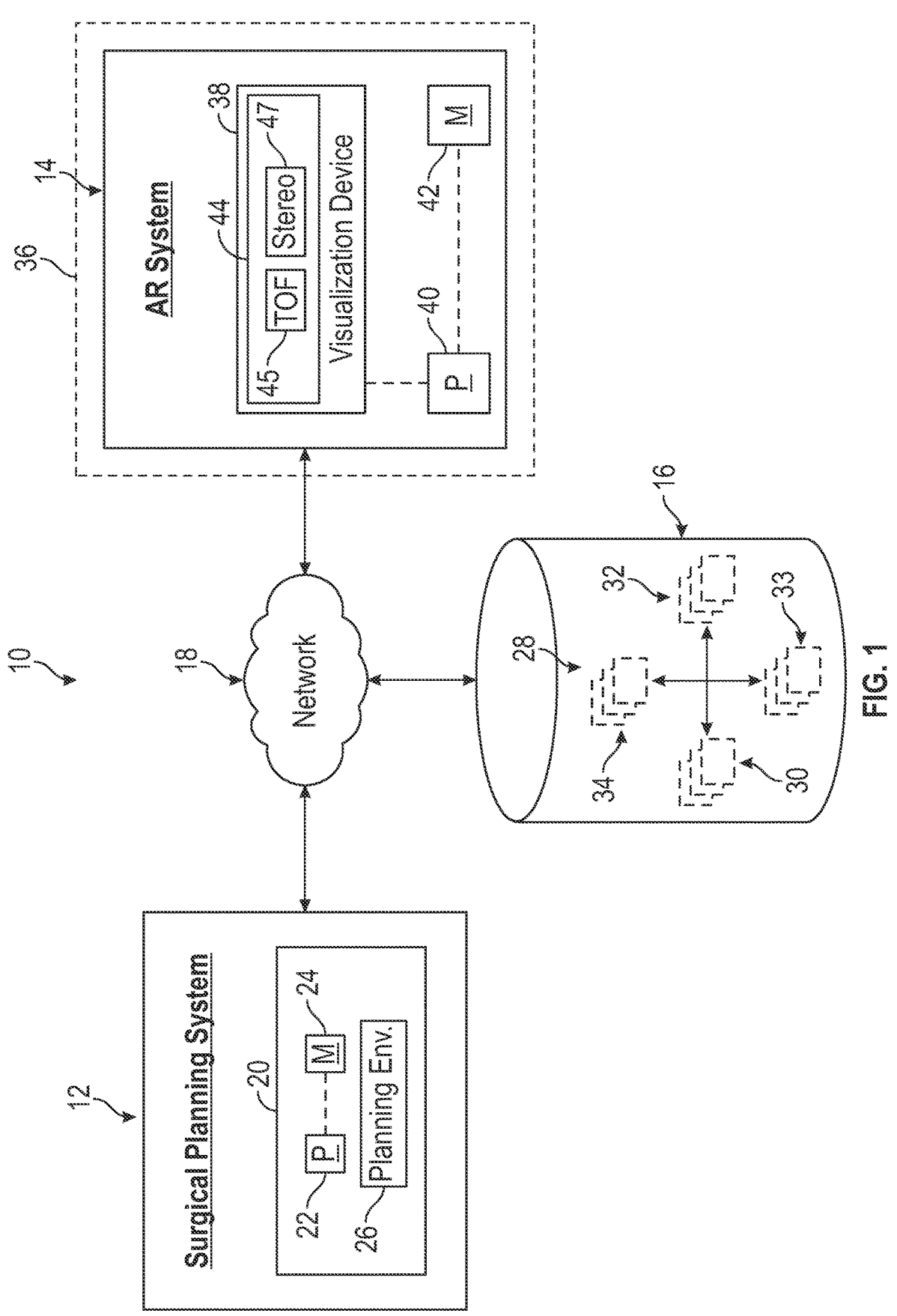
FIG. 1 schematically illustrates an exemplary orthopedic surgical system.

This disclosure describes orthopedic surgical systems and methods for providing augmented reality visualization during surgical procedures, such as arthroplasty procedures, for example. The disclosed surgical systems and methods utilize augmented reality navigation and visualization techniques to transfer aspects of a preoperative surgical plan to the intraoperative anatomy of a patient.

In some implementations, the orthopedic surgical systems and methods of this disclosure may be utilized to achieve accurate alignment of a surgical positioning object, such as a guide pin for guiding reaming procedures, between the preoperative surgical plan and the intraoperative anatomy associated with the actual surgical site. Augmented reality may be utilized to achieve visualization of both an entry point and a drilling trajectory of the surgical positioning object in a manner that avoids occluding the intraoperative anatomy during the procedure. These and other features of this disclosure are further detailed below.

An augmented reality system for a surgical system according to an exemplary aspect of this disclosure may include an augmented reality visualization device and a processor. The processor may be programmed to control the augmented reality visualization device to provide an augmented reality environment relative to a patient's anatomy. The processor may be further programmed to allow a user to interface with the augmented reality environment for intraoperatively achieving a desired entry point and a desired trajectory of a surgical positioning object relative to the patient's anatomy.

In a further implementation, the processor is further programmed to control the augmented reality visualization device to virtually indicate the desired entry point with a virtual object.

In a further implementation, the virtual object includes a virtual crosshair.

In a further implementation, the processor is further programmed to control the augmented reality visualization device to virtually indicate the desired trajectory with a directional indictor or an angular difference indicator.

In a further implementation, the directional indicator or the angular difference indicator is overlaid onto a trajectory marker that is connected to the surgical positioning object.

In a further implementation, the processor is further programmed to control the augmented reality visualization device to perform a registration process for registering a virtual bone model to the patient's anatomy within the augmented reality environment.

In a further implementation, the processor is further configured to control the augmented reality visualization device to present a plurality of registration reference points within the augmented reality environment. Each of the plurality of registration reference points visually indicates a location where the user should physically touch the patient's anatomy in order to initialize an approximation of the virtual bone model to the patient's anatomy.

In a further implementation, the processor is further programmed to control the augmented reality visualization device to visually indicate an accuracy between an actual trajectory and the desired trajectory of the surgical positioning object within the augmented reality environment.

In a further implementation, the processor is further programmed to control the augmented reality visualization device to visually indicate the accuracy by altering a color of a virtual indicator presented within the augmented reality environment.

In a further implementation, the surgical positioning object is a surgical guide pin.

A surgical method according to an exemplary aspect of this disclosure may include intraoperatively demarcating a desired entry point and a desired trajectory of a surgical positioning object within an augmented reality environment produced by an augmented reality system. A visual indication of an accuracy between an actual trajectory and the desired trajectory of the surgical positioning object may be provided within the augmented reality environment.

In a further implementation, intraoperatively demarcating the desired entry point includes presenting a virtual crosshair within the augmented reality environment.

In a further implementation, intraoperatively demarcating the desired trajectory includes presenting a virtual trajectory within the augmented reality environment.

In a further implementation, providing the visual indication of the accuracy includes presenting a directional indicator within the augmented reality environment.

In a further embodiment, providing the visual indication of the accuracy includes presenting an angular difference indicator within the augmented reality environment.

In a further embodiment, the visual indication of the accuracy is virtually overlaid onto a trajectory marker that is connected to the surgical positioning object.

In a further implementation, the trajectory marker is configured to digitize the actual trajectory of the surgical positioning object.

In a further implementation, the method includes, prior to intraoperatively demarcating the desired entry point and the desired trajectory, registering a virtual bone model to a patient's anatomy within the augmented reality environment.

In a further implementation, the surgical positioning object is a surgical guide pin.

A surgical method according to another exemplary aspect of this disclosure may include positioning a tip of a surgical guide pin at a location of a bone surface of an anatomy that is indicated by a virtual crosshair, preparing an indentation at the location, pivoting the surgical guide pin about a pivot point established by the indentation, and aligning an actual trajectory of the surgical guide pin to a virtual trajectory of the surgical guide pin within an augmented reality environment.

FIG. 1 illustrates an exemplary orthopedic surgical system 10 (hereinafter referred to as "the system 10") according to an exemplary embodiment of this disclosure. The system 10 may be used for creating, editing, reviewing, and/or executing surgical plans, such as surgical plans for performing arthroplasty procedures to repair a joint, for example. The teachings of this disclosure are not intended to be limited to any particular joint of the human musculoskeletal system and are therefore applicable to the shoulder, knee, hip, ankle, wrist, etc.

The system 10 may include, among other subsystems, a surgical planning system 12, an augmented reality (AR) system 14, a storage system 16, and a network 18. The system 10 may include a greater or fewer number of subsystems within the scope of this disclosure. As discussed in greater detail below, the surgical planning system 12 may be configured for allowing one or more users to preoperatively create a surgical plan, and the AR system 14 may be configured to allow the one or more users to intraoperatively review, edit, update, verify, and/or execute the preoperative surgical plan. In an embodiment, the AR system 14 is used to transfer certain aspects of the preoperative surgical plan to the surgical site, including but not limited to aspects such as a desired implant size and positioning, and a desired guide pin placement for guiding reaming procedures that are necessary to prepare the native anatomy for receiving the desired implant size and positioning.

In this disclosure, the term "augmented reality" is intended to refer to the ability to provide interactive experiences in which real objects (e.g., a patient's anatomy) that reside within a given environment may be augmented with computer-generated perceptual information across one or more sensory modalities (e.g., visual, auditory, haptic, etc.). In addition, the term "augmented reality" is intended to be inclusive of aspects of mixed reality, virtual reality, extended reality, holographic projecting, etc.

The surgical planning system 12 may be configured for preoperatively planning surgical procedures. The preoperative planning provided by the surgical planning system 12 may include, but is not limited to, features such as constructing a virtual model of a patient's anatomy, identifying landmarks within the virtual model, selecting and orienting virtual implants within the virtual model, identifying optimal insertion points and trajectories for guiding surgical reaming procedures within the virtual model, etc. An exemplary surgical planning system suitable for use as the surgical planning system 12 of the system 10 is the Virtual Implant Positioning™ (VIP) System available from Arthrex, Inc.

The surgical planning system 12 may include a computing device 20 that includes a processor 22 operably coupled to a memory 24. The computing device 20 may be a single computer or a multitude of computers configured to process software instructions serially or in parallel. The computing device 20 may be configured to communicate with the AR system 14 and/or other computing devices over the network 18.

The processor 22 can be a custom made or commercially available processor, central processing unit (CPU), or generally any device for executing software instructions. The memory 24 can include any one or combination of volatile memory elements and/or nonvolatile memory elements. The processor 22 may be operably coupled to the memory 24 and may be configured to execute one or more programs stored in the memory 24 based on various inputs received from other devices or data sources.

In an embodiment, the processor 22 of the computing device 20 may be operable to access and locally and/or remotely execute a planning environment 26 for creating, editing, executing, and/or reviewing one or more surgical plans 34 during preoperative, intraoperative, and/or postoperative phases of a surgery. The planning environment 26 may be a standalone software package or may be incorporated into another surgical tool. The planning environment 26 may, for example, provide a display or visualization of one or more bone models 30 and related images and one or more implant models 32 and related images via one or more graphical user interfaces (GUI). Each bone model 30, implant model 32, and related images and other information may be stored in one or more files or records according to a specified data structure.

The planning environment 26 may include various modules for performing the desired planning functions. In an embodiment, the planning environment 26 includes a data module for accessing, retrieving, and/or storing data concerning the surgical plans 34, a display module for displaying the data (e.g., within a GUI), a spatial module for modifying the data displayed by the display module, and a comparison module for determining one or more relationships between selected bone models and selected implant models, for example. However, a greater or fewer number of modules may be utilized, and/or one or more of the modules may be combined to provide the disclosed functionality.

The storage system 16 may be configured to store or otherwise provide data from/to the surgical planning system 12 and the AR system 14. The storage system 16 may be a storage area network device (SAN) configured to communicate with the surgical planning system 12 and the AR system 14 over the network 18, for example. Although shown as a separate device, the storage system 16 could be incorporated within or directly coupled to the computing device 20 of the surgical planning system 12. The storage system 16 may be configured to store one or more of computer software instructions, data, database files, configuration information, etc.

In an embodiment, the surgical planning system 12 includes a client-server architecture configured to execute computer software on the computing device 20, which is accessible using either a thin client application or a web browser executed on the computing device 20. The computing device 20 may load the computer software instructions from either local storage or from the storage system 16 into the memory 24 and may execute the computer software using the processor 22.

The system 10 may further include one or more databases 28. The databases 28 may be stored at a central location, such as the storage system 16, for example. Each database 28 may be a relational database configured to associate one or more bone models 30, one or more implant models 32, and one or more transfer models 33 to each other and/or to a surgical plan 34. Each surgical plan 34 may be associated with a respective patient. Each bone model 30, implant model 32, transfer model 33, and surgical plan 34 may be assigned a unique identifier or database entry or record within the database 28. The database 28 may be configured to store data corresponding to the bone models 30, implant models 32, transfer models 33, and surgical plans 34 in one or more database records or entries, and/or may be configured to link or otherwise associate one or more files corresponding to each respective bone model 30, implant model 32, transfer model 33, and surgical plan 34. Bone models 30 stored in the database(s) 28 may correspond to respective patient anatomies from prior surgical cases, and may be arranged into one or more predefined categories such as sex, age, ethnicity, defect category, procedure type, etc.

Each bone model 30 may include information obtained from one or more medical devices or tools, such as a computerized tomography (CT), magnetic resonance imaging (MRI) machine and/or X-ray machine, that obtains one or more images of a patient. The bone model 30 may include one or more digital images and/or coordinate information relating to an anatomy of the patient that can be obtained or derived from the medical device(s).

Each implant model 32 may include coordinate information associated with a predefined implant design. The planning environment 26 may incorporate and/or interface with one or more modeling packages, such as a computer aided design (CAD) package, to render the models 30, 32 as two-dimensional (2D) and/or three-dimensional (3D) volumes or constructs. The predefined design may correspond to one or more components. The implant models 32 may correspond to implants and components of various shapes and sizes. Each implant may include one or more components that may be situated at a surgical site including screws, anchors, grafts, etc. Each implant model 32 may correspond to a single component or may include two or more components that may be configured to establish an assembly. Each bone model 30, implant model 32, and transfer model 33 may correspond to 2D and/or 3D geometry and may be utilized to utilized to generate a wireframe, mesh, and/or solid construct in a graphical display.

Each transfer model 33 may correspond to various instrumentation and devices used to implement each surgical plan 34, including preparing the surgical site and securing one or more implants to bone or other tissue to restore functionality to the respective joint. Each of the transfer models 33 may be associated with a respective surgical instrument or device (e.g., guide pins, transfer guides, etc.) and/or a respective implant model 32. Each transfer model 33 may include coordinate information associated with a predefined instrument design.

The surgical plan 34 may be associated with one or more surgical positioning objects such as a guide pin (e.g., guide wire or Kirschner wire) dimensioned to be secured in tissue to position and orient various instrumentation, devices and/or implants. In some implementations, the surgical positioning objects are used to guide reaming procedures that are necessary for preparing a patient's anatomy for receiving a desired implant. Exemplary transfer models 33 may be configured to preoperatively establish a virtual entry or insertion position and virtual trajectory axis of one or more surgical positioning objects relative to one or more bone models 30. The virtual positions may be associated with a specified insertion point and trajectory of the surgical positioning object relative to the patient anatomy (as represented by the bone model(s) 30). The virtual trajectory axis may extend through the virtual position and may be associated with a specified orientation of the surgical positioning object relative to the patient anatomy for any given surgical plan 34.

The planning environment 26 may be configured to set the virtual position and/or virtual axis of the surgical positioning object in response to placement of a respective implant model 32 relative to the bone model 30 and associated patient anatomy. The virtual position and/or virtual axis may be set and/or adjusted automatically based on a position and orientation of the selected implant model 32 relative to the selected bone model 30 and/or in response to user interaction with the planning environment 26.

Each surgical plan 34 may be associated with one or more of the bone models 30, implant models 32, and transfer models 33. The surgical plan 34 may include one or more revisions to the bone model 30, information relating to a desired position of an implant model 32 relative to the original and/or revised bone model 30, and information (e.g., a desired entry point and trajectory) related to a desired position of a surgical positioning object of a transfer model 33 relative to the original and/or revised bond model 30. The surgical plan 34 may include coordinate information relating to the revised bone model and a relative position of the implant model 32 and/or transfer model 33 in predefined data structure(s). Revisions to each bone model 30 and surgical plan 34 may be stored in the database 28 automatically and/or in response to user interaction with the surgical planning system 12.

One or more surgeons and other users may be presented with the planning environment 26 via the computing device 20 or another computer operably linked to the surgical planning system 12. The users may simultaneously access each bone model 30, implant model 32, transfer model 33, and surgical plan 34 stored in the database(s) 28. Each user may interact with the planning environment 26 to create, view, and/or modify various aspects of the surgical plan 34. The computing device 20 may be configured to store local instances of the bone models 30, implant models 32, transfer models 33, and/or surgical plans 34, which may be synchronized in real-time or periodically with the database(s) 28.

The AR system 14 may allow one or more users to intraoperatively review, edit, update, verify, and/or execute the surgical plan 34 for a given patient. In an embodiment, the AR system 14 provides the one or more users with an interactive surgical experience in which real objects that reside within a healthcare facility (e.g., a hospital, surgery center, etc.), and more specifically within an operating room 36 of the healthcare facility, are augmented with computer-generated perceptual information across one or more sensory modalities. Therefore, when using the AR system 14 prior to or during a surgical procedure, the user(s) may perceive and interact with images that include both real and virtual objects.

The AR system 14 may include, among other things, a visualization device 38, a processor 40, and a memory 42 operably coupled to the processor 40. The visualization device 38 may be configured to communicate with the surgical planning system 12, the storage system 16, and/or other AR visualization devices over the network 18. The processor 40 and the memory 42 may either be provided on or within the visualization device 38 or separate from the visualization device 38, such as within a computing device that is operably connected to the visualization device 38, for example.

In an embodiment, the visualization device 38 is a head-mounted display or head-up display that can be worn on the head of a user. However, other types of visualization devices are also contemplated within the scope of this disclosure. An exemplary visualization device suitable for use within the AR system 14 of the system 10 is the Microsoft HOLOL- ENS™ headset, available from Microsoft Corporation. In other embodiments, the AR system 14 could include multiple different visualization devices capable of being used together for providing the interactive surgical experience.

The processor 40 of the AR system 14 can be a custom made or commercially available processor, central processing unit (CPU), or generally any device for executing software instructions. The memory 42 can include any one or combination of volatile memory elements and/or non-volatile memory elements. The processor 40 may be operably coupled to the memory 42 and may be programmed to execute one or more programs stored in the memory 42 based on various inputs received from other devices or sources. For example, the processor 40 may be programmed to execute various software instructions stored on the memory 42 for providing interactive surgical experiences. In an embodiment, as is discussed in greater detail below, the processor 40 is programmed to control the visualization device 38 for presenting one or more AR environments to the user. The AR environment may include various user interfaces, menus, virtual objects, etc. for transferring aspects of the preoperative surgical plan 34 to the intraoperative anatomy.

The processor 40 may be further programmed to selectively access the relevant bone models 30, implant models 32, transfer models 33, and surgical plans 34 for a particular patient from the database(s) 28 of the storage system 16. In some embodiments, certain aspects associated with the bone model 30, implant model 32, and/or surgical plan 34 for a particular patient may be stored directly within the memory 42, which may be synchronized in real-time or periodically with the database(s) 28, and may be executed by the processor 40. In another embodiment, certain aspects and functionalities associated with the surgical planning system 12 may be stored on the memory 42 and may be executed by the processor 40.

The visualization device 38 may additionally include a sensor system 44 that includes a plurality of sensors (e.g., images sensors, optical sensors, depth sensors, motion sensors, etc.). The sensor system 44 may be configured to collect data that can be processed by the processor 40 in order to present, position, move, and/or adjust virtual objects within the AR environment relative to the real environment of the operating room 36. In an embodiment, the sensor system 44 is capable of detecting hand gestures, audible commands, etc. that can be processed by the processor 40 in order to interact with the virtual objects being projected by the visualization device 38.

In an embodiment, the sensor system 44 includes both a time-of-flight camera 45 and a visible light stereo camera 47. The time-of-flight camera 45 and the visible light stereo camera 47 may each be operably coupled to the visualization device 38. Image data from the time-of-flight camera 45 and the visible light stereo camera 47 may be processed by the processor 40 for conducting an inside-out registration process that does not require the use of fiducial markers to be placed on the patient's anatomy. The inside-out registration process may include performing a 3D reconstruction of the captured imagery and then registering preoperative image data to the patient's anatomy.

In an embodiment, the processor 40 of the AR system 14 may be programmed to execute a stereo transformer model for providing stereo reconstruction of the captured imagery. The stereo transformer model may utilize both self-attention within single images and cross-attention between multiple images to identify pixel correspondence between the captured imagery. The attention mechanism of the stereo transformer model may allow the model to mitigate ambiguity of feature correspondence on texture-less surfaces by attending to discernible features in proximity to the point of interest. The stereo transformer model may thus produce reasonable dense reconstruction even on relatively texture-less bone surfaces.

Figure 2:
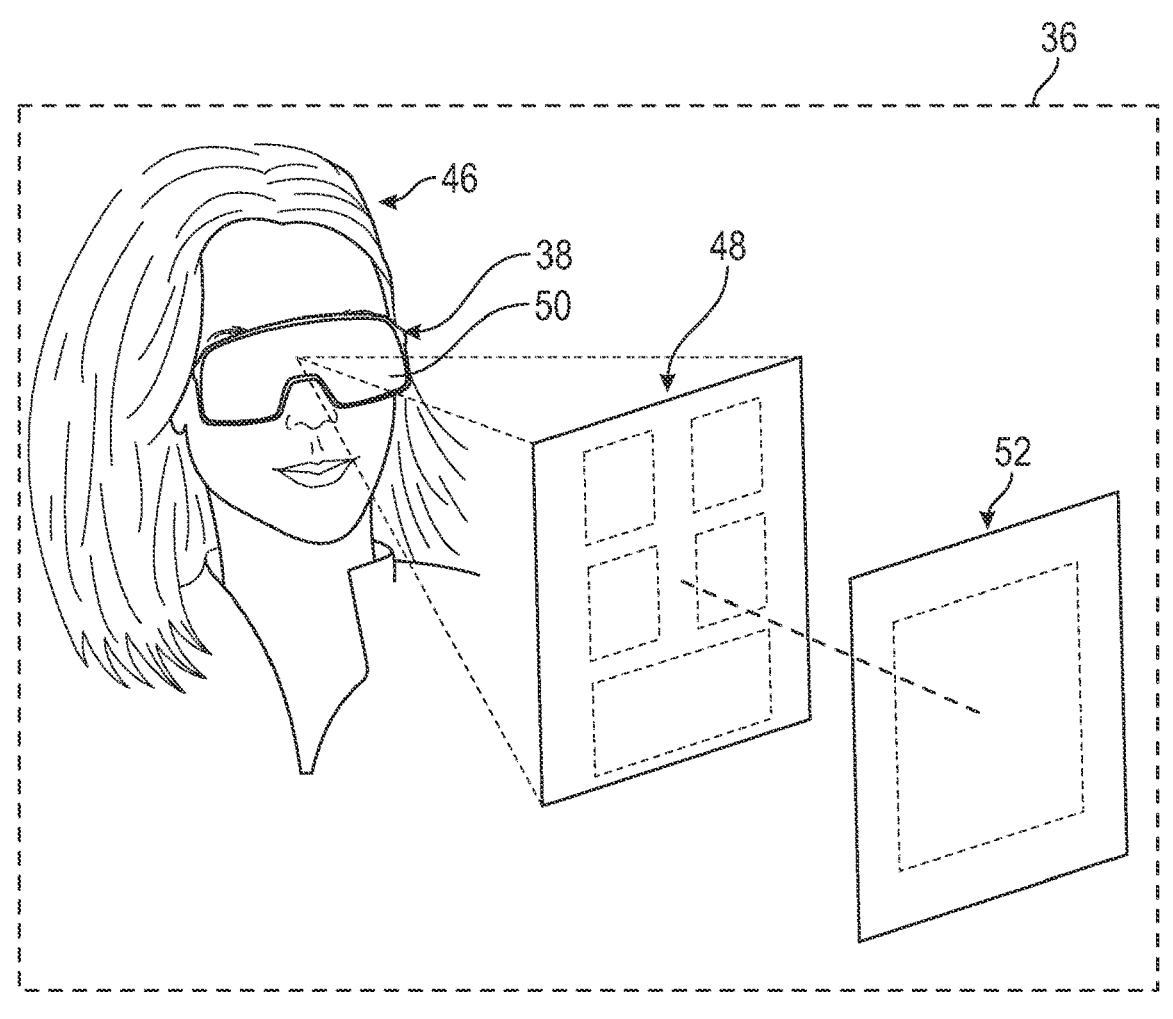
FIG. 2 schematically illustrates aspects of an augmented reality system of the orthopedic surgical system of FIG. 1.

Referring now to FIG. 2, the visualization device 38 of the AR system 14 may be worn by a user 46 (e.g., a surgeon or other healthcare provider) and is configured to provide an AR environment 48 that may be overlaid onto real objects 52 (e.g., the patient's anatomy, an operating table, etc.) that are located within the operating room 36. Thus, the visualization device 38 allows the user 46 to intraoperatively visualize both virtual and real objects within the operating room 36.

The AR environment 48 may be projected as a holographic image onto a screen 50 of the visualization device 38 and may present, among other things, one or more user interfaces that include virtual details associated with one or more surgical plans 34 that have been preoperatively planned using the surgical planning system 12. Once projected, the AR environment 48 is visibly perceptible by the user 46 in the foreground of the operating room 36, with the real objects 52 appearing in the background of the projected virtual imagery. As further discussed below, the user 46 may visualize and interact with the AR environment 48 for executing the surgical plan 34 for a given patient during a live surgical procedure.

Figure 3:
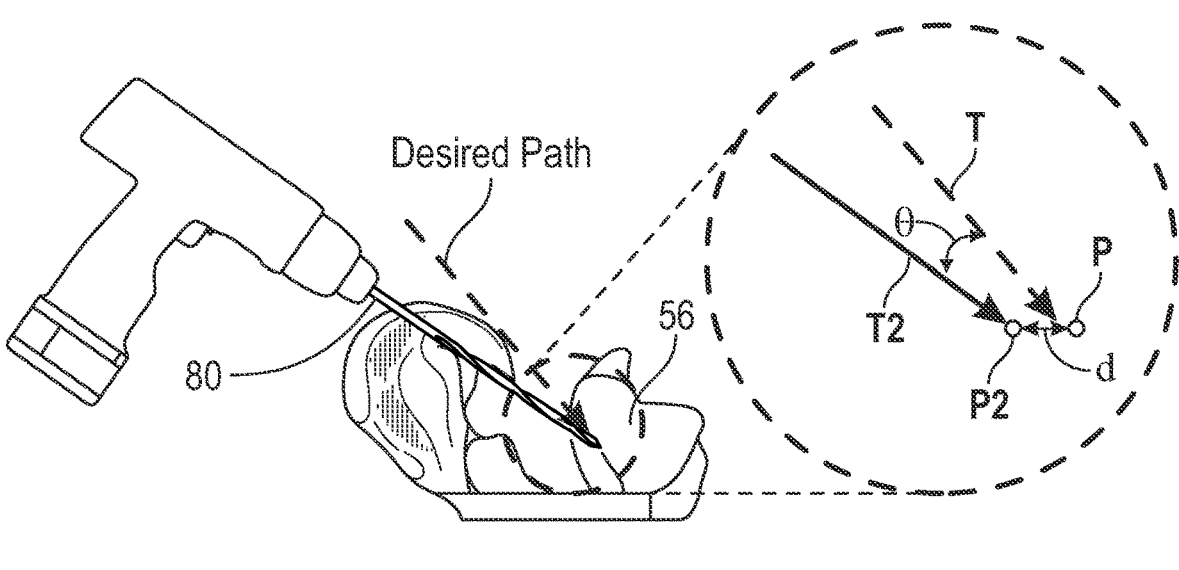
FIG. 3 schematically illustrates a targeting process for guiding positioning of a surgical positioning object.

The AR environment 48 produced by the AR system 14 may be utilized to transfer certain aspects of the preoperative surgical plan 34 to the intraoperative anatomy during an orthopedic procedure. For example, as further detailed below, the user can utilize the AR environment 48 for performing a targeting process for positioning a surgical positioning object (e.g., a guide pin 80) within an anatomy 56 of a respective patient. In some implementations, this targeting process may include indicating a desired entry point P and a desired trajectory T of a guide pin 80 within the AR environment 48. FIG. 3 visually depicts such a targeting process for the guide pin 80. Decomposing the targeting process into discrete steps enables the entry point positional accuracy (in millimeters) and trajectory rotational accuracy (in degrees) metrics to be decoupled from one another and used to evaluate drilling task performance during the orthopedic procedure.

A first step of positioning the guide pin 80 at the desired entry point P of the anatomy 56 may be referred to as establishing a desired translational aspect of the guide pin 80. A translation distance d may refer to the distance (e.g., in mm) between the desired entry point P of the guide pin 80 and an actual position P2 of a tip of the guide pin 80.

A second step of establishing the desired trajectory T of the guide pin 80 may be referred to as establishing a rotational trajectory aspect of the guide pin 80. Rotation may refer to an amount of rotation $\Theta$ (e.g., in degrees) between the desired trajectory T and an actual trajectory T2 of the guide pin 80.

FIG. 4, with continued reference to FIGS. 1-3, schematically illustrates an exemplary surgical method 100 that can be performed using the system 10 for planning and executing orthopedic surgical procedures. The surgical method 100 may be utilized preoperatively and intraoperatively to create, edit, and execute a respective surgical plan 34. In an embodiment, the surgical method 100 is utilized to perform an arthroplasty procedure for restoring functionality to a shoulder joint or any other joints.

Although the surgical method 100 is described herein with reference to repairing a defect in a glenoid during a shoulder arthroplasty, it should be understood that the surgical method 100 could be utilized in other locations of the patient and for other orthopedic surgical procedures. Thus, fewer or additional steps than are recited below could be performed within the scope of this disclosure. Moreover, the recited order of steps is not intended to limit this disclosure.

The orthopedic surgical procedure may be preoperatively planned using the surgical planning system 12 of the system 10 at block 102. The preoperative planning may include acquiring images of a patient's anatomy, constructing a virtual model of a patient's anatomy, identifying landmarks within the virtual model, selecting and orienting virtual implants within the virtual model, identifying and marking the desired entry point P and the desired trajectory T of the guide pin 80 for guiding reaming procedures for reaming the anatomy 56, etc., and results in the creation of the surgical plan 34 for the respective patient.

Figure 5:
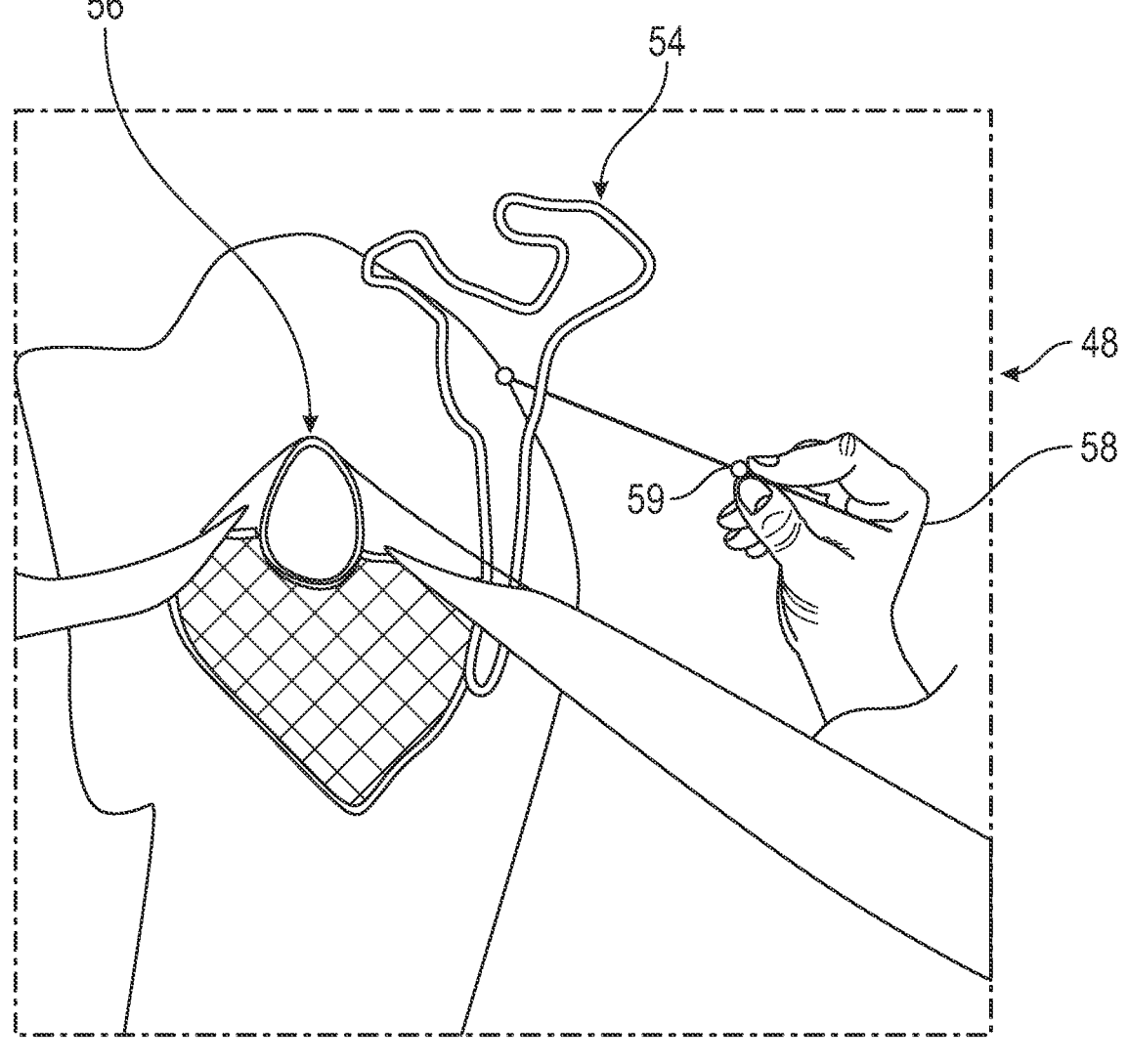
FIG. 5 illustrates an augmented reality environment that can be provided by an augmented reality system of an orthopedic surgical system.

The user may intraoperatively generate the AR environment 48 using the visualization device 38 of the AR system 14 in order to augment real objects that reside within the operating room 36 of a healthcare facility with computer-generated perceptual information across one or more sensory modalities at block 104. An exemplary AR environment 48 is illustrated in FIG. 5. The AR environment 48 may include various user interface modules or menus that are designed to present a multitude of information to the user during a given surgical procedure. Although a specific arrangement of user interface modules are shown in the figures of this disclosure, other arrangements are further contemplated within the scope of this disclosure. Therefore, the specific size, positioning, and overall arrangement of the AR modules shown herein are not intended to limit this disclosure.

During step 104 of the method 100, the user may register a virtual bone model 54 to the anatomy 56. In an embodiment, the AR environment 48 includes a registration module that allows the user to overlay the virtual bone model 54 (e.g., derived from the surgical plan 34) on the patient's actual anatomy 56. The registration module may be configured to allow the user to interact with the AR environment 48 prior to and/or during the surgical procedure. A user may interact with the selectable buttons, menus, widgets, etc. using hand gestures or audible commands, for example. For example, the user may use his/her hand 58 to interact with a cursor 59 within the AR environment 48 in order to position the virtual bone model 54 at a desired position relative to the anatomy 56.

Figure 6:
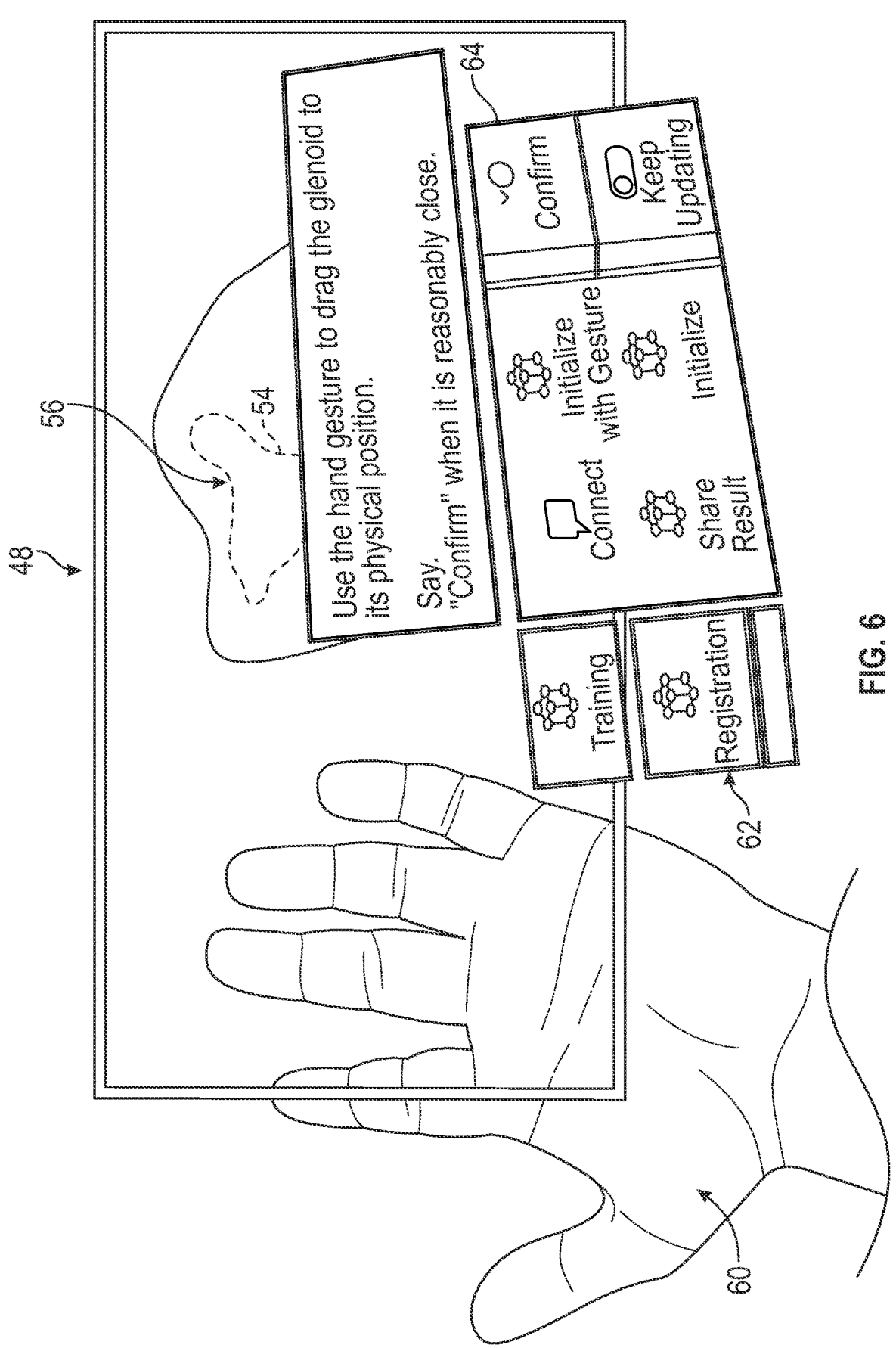
FIG. 6 illustrates exemplary aspects of a registration module of the augmented reality environment of FIG. 5.

Once the desired position is achieved, the user may perform a hand gesture 60 to cause a registration menu 62 to be presented within the AR environment 48 (see FIG. 6). The user can confirm completion of the overlay by either pressing a confirm button 64 of the registration menu 62 or by using an audible command.

Figure 7:
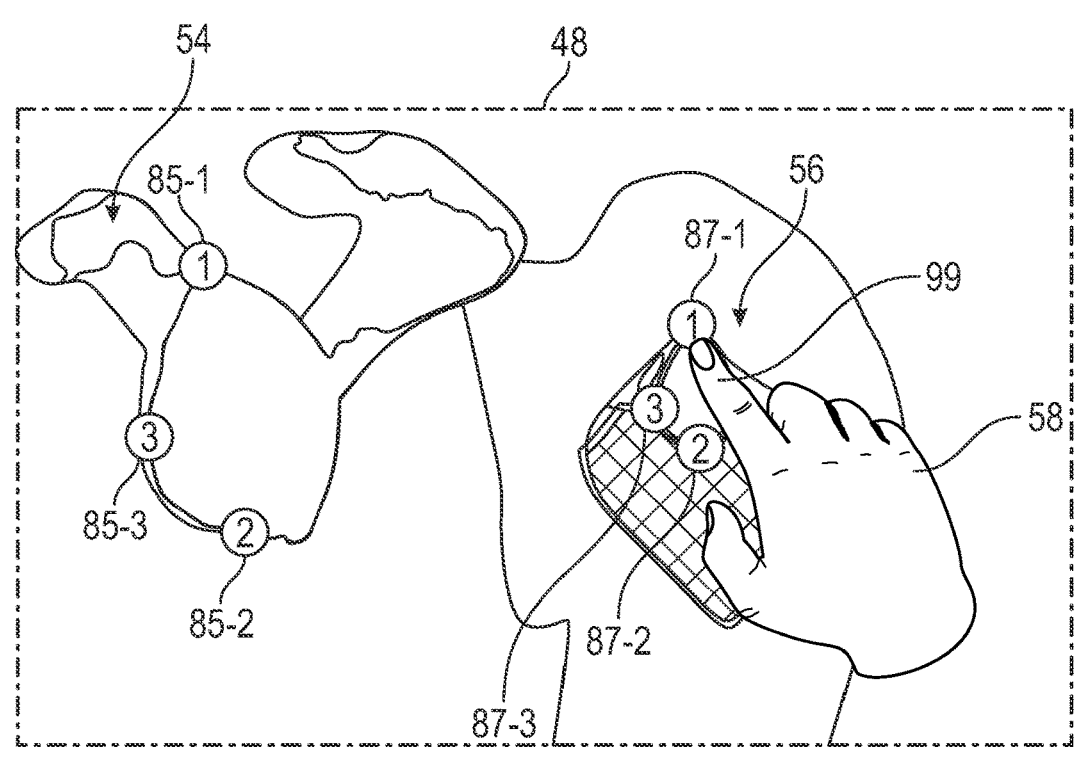
FIGS. 7 and 8 illustrate an exemplary initialization step of a multi-step registration process that may be performed by an augmented reality system of an orthopedic surgical system.

In other implementations, the registration module of the AR environment 48 may be configured allow the user (or a group of users having operably connected visualization devices) to register the virtual bone model 54 to the anatomy 56 using a multi-step registration process. An initialization step of the multi-step registration process may first be performed in order to approximate a position and orientation of the virtual bone model 54 to the anatomy 56. During the initialization step, the system 10 may present a plurality of registration reference points 85 on the virtual bone model 54 (see FIG. 7). Although three registration reference points 85-1 (e.g., a superior reference point), 85-2 (e.g., an inferior reference point), and 85-3 (e.g., an anterior/posterior reference point) are shown, a greater or fewer number of registration reference points 85 may be provided relative to the virtual bone model 54 within the AR environment 48. Moreover, a person of ordinary skill in the art would understand that the registration reference points 85 could be presented at any location of the virtual bone model 54.

Figure 8:
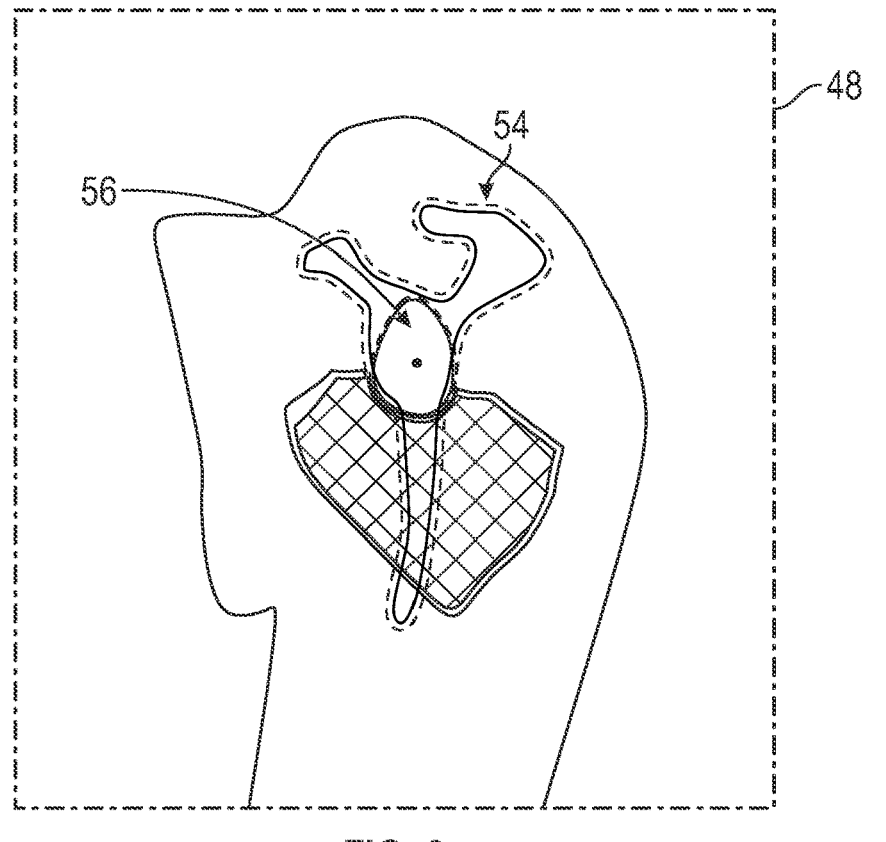

The registration reference points 85-1, 85-2, 85-3 may visually indicate the locations where the user(s) should physically touch the anatomy 56 in order to initialize the approximation of the virtual bone model 54 to the anatomy 56. The registration reference points 85-1, 85-2, 85-3 essentially define a reference plane in the physical space defined by the patient site for orienting and positioning the virtual bone model 54 relative to the anatomy 56. As schematically depicted, the user(s) may physically touch the anatomy 56 at multiple touch points 87-1, 87-2, and 87-3 that correspond, as close as possible, to the locations indicated by the registration reference points 85-1, 85-2, 85-3 (see FIG. 7). The touch points 87-1, 87-2, and 87-3 may be touched using a finger 99 of the user's hand 58, a pointer tool, or some other suitable object. The system 10 may then complete the initialization step by loosely aligning a silhouette of the virtual bone model 54 to corresponding features of the anatomy 56 (see FIG. 8).

Figure 9:
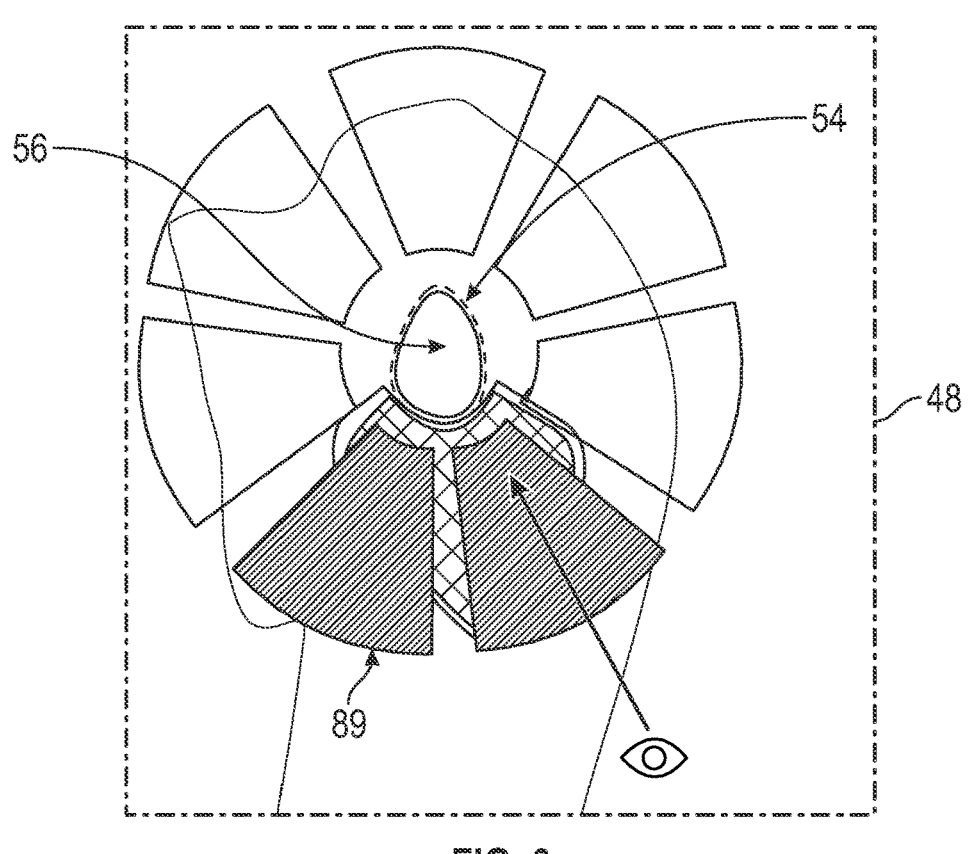
FIGS. 9 and 10 illustrate an exemplary 3D scanning step of a multi-step registration process that may be performed by an augmented reality system of an orthopedic surgical system
Figure 10:
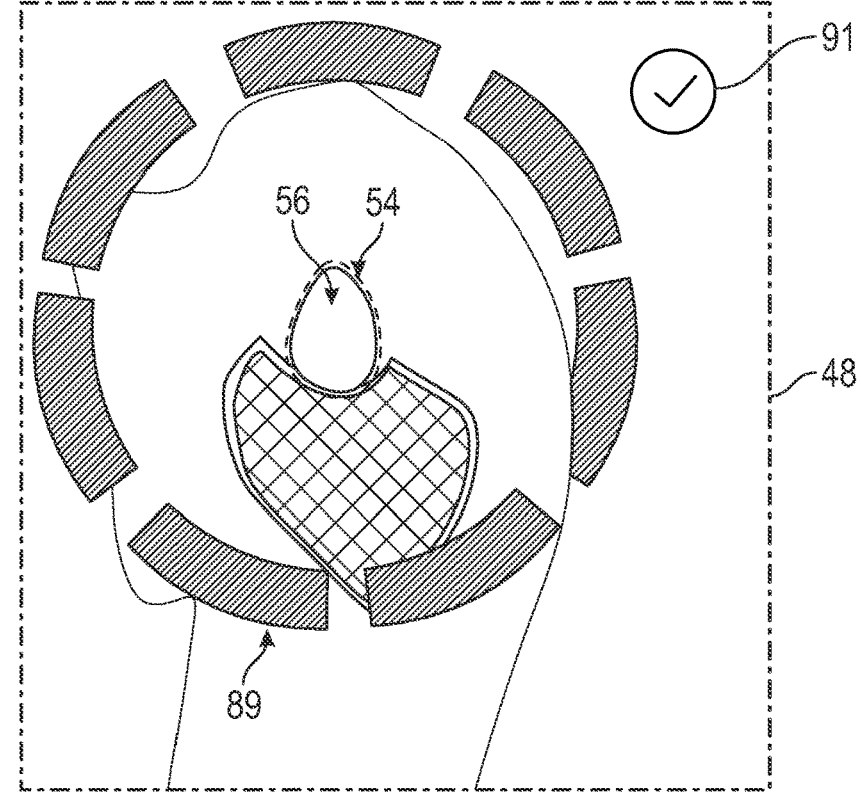

A 3D scanning step of the multi-step registration process may next be performed in order to capture, segment, and classify anatomic volumes using a 3D point cloud mesh of the anatomy 56 associated with the patient site. During the initialization step, the system 10 may analyze the anatomy 56 from various angles in order to three-dimensionally reconstruct the anatomy 56 in an effort to improve the positional accuracy of the virtual bone model 54 relative to the anatomy 56. The system 10 may present a progress indicator 89 within the AR environment 48 as the 3D scanning is being performed (see FIG. 9). The progress indicator 89 may overlay the anatomy 56 and may be configured to visually indicate the progression of the 3D scanning operation to the user(s). Upon completion of the 3D scanning step, the system 10 may present a graphic 91 (e.g., checkmark, etc.) within the AR environment 48 at a location adjacent to the progress indicator 89 for visually indicating to the user(s) that the 3D scanning has completed (see FIG. 10).

The initialization and the 3D scanning operations can produce the registration of the virtual bone model 54 to the anatomy 56. After completing the initialization, 3D scanning, and registration, the multi-step registration process of the method 100 may continuously analyze a camera feed from the visualization device(s) 38 to maintain accurate blending of virtual structures (spatial anchoring) based at least on motion and pose of the visualization device(s) 38.

After registering the virtual bone model 54 to the anatomy 56, the user may utilize the AR environment 48 for transferring certain aspects of the preoperative surgical plan 34 to the intraoperative anatomy 56. For example, as further detailed below, the user can utilize the AR environment 48 for performing the targeting process for accurately positioning a surgical positioning object (e.g., the guide pin 80) within the anatomy 56.

Figure 11:
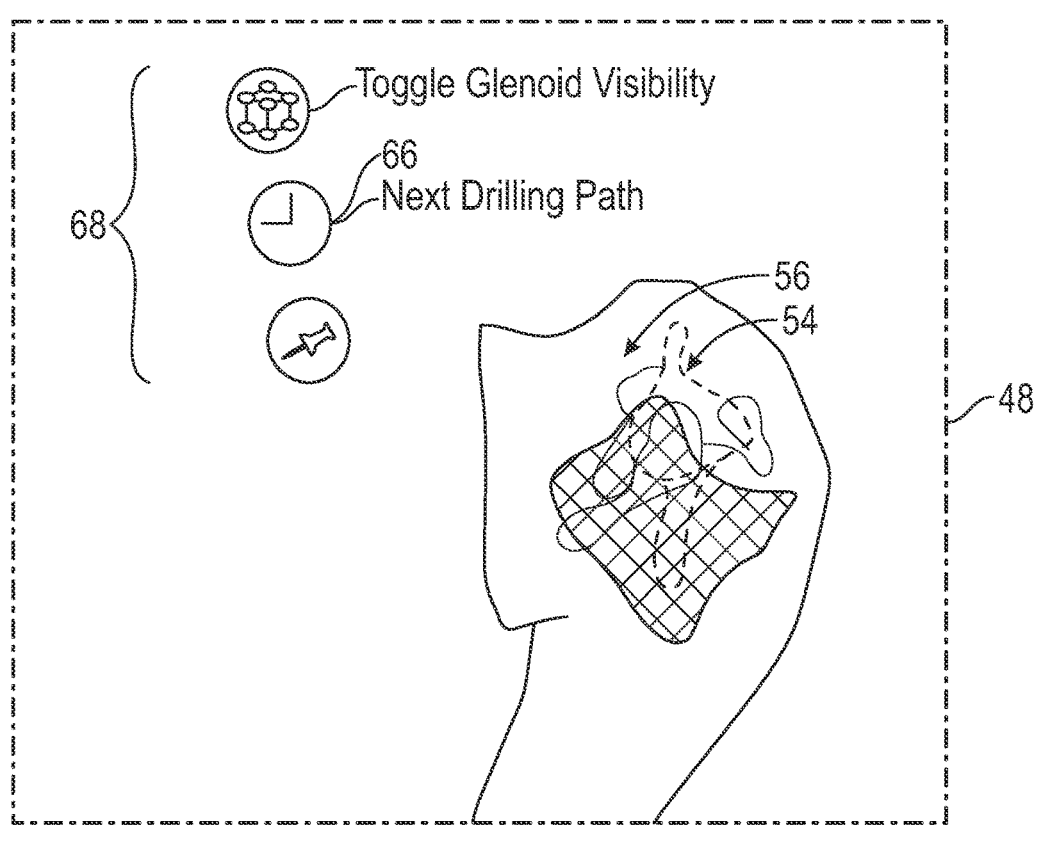
FIG. 11 illustrates another augmented reality environment that can be provided by an augmented reality system of an orthopedic surgical system.

Referring again to FIG. 4, the user may next initiate a guide pin placement module of the AR environment 48 at block 106 of the method 100. The guide pin placement module may be used to accurately set the entry position and trajectory of the guide pin 80 to be placed in the patient's anatomy 56 (e.g., glenoid) for guiding placement of an implant (e.g., a glenoid baseplate). The guide pin placement module of the AR environment 48 may be initialized by actuating a guide pin placement button 66 that may be presented within another menu 68 of the AR environment 48 (see, e.g., FIG. 11).

Figure 12:
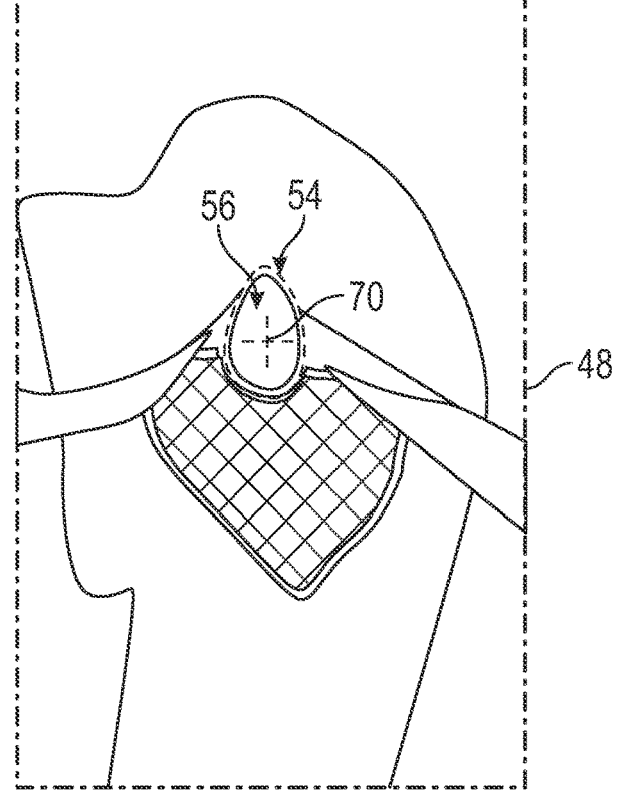
FIG. 12 illustrates exemplary aspects of a transfer module of an augmented reality environment.

A virtual crosshair 70 (or some other visual indicator) may be displayed over the anatomy 56 within the AR environment 48 at block 108 (see FIG. 12). The location of the virtual crosshair 70 may be derived from the information stored in the preoperative surgical plan 34. The virtual crosshair 70 may identify the desired entry point P of the guide pin 80 and thus provides visualization of the optimal insertion location of the guide pin 80.

Figure 13:
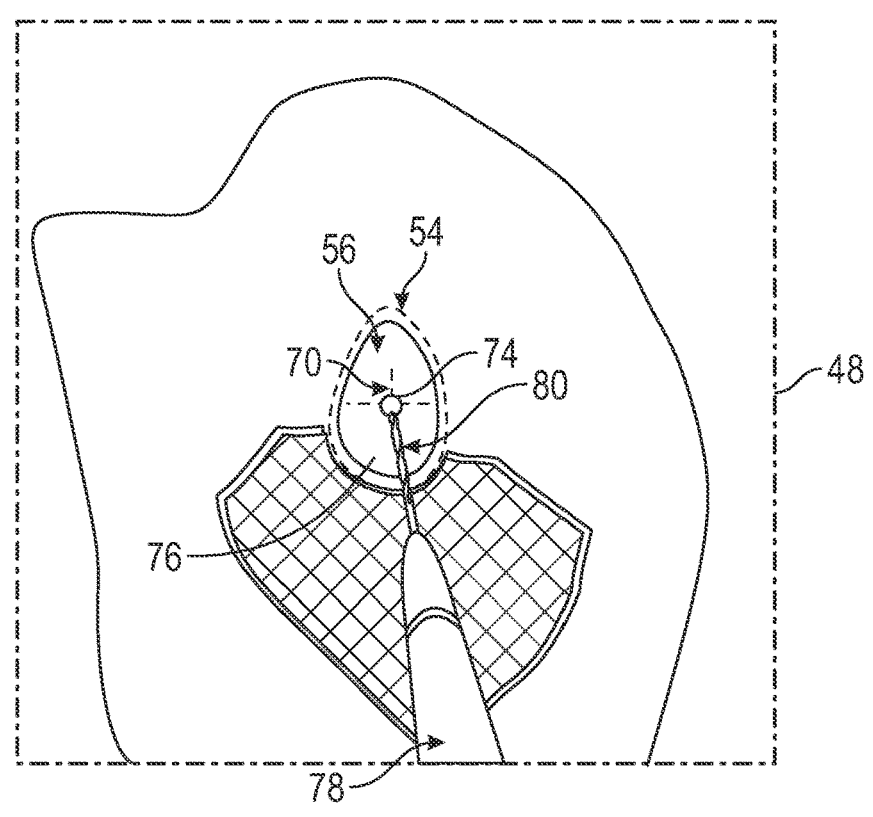
FIG. 13 illustrates additional aspects of a transfer module of an augmented reality environment.

Next, at block 110, the user may prepare a shallow dent 74 (e.g., an indentation) in a bone surface 76 (e.g., a glenoid surface) of the anatomy 56 at the location of the virtual crosshair 70 using a drill tip of the guide pin 80 (see FIG. 13). The shallow dent 74 may act as a pivot point for adjusting a rotational position, and thus the trajectory, of the guide pin 80 relative to the bone surface 76. The guide pin 80 may be held by a powered surgical instrument, such as a surgical drill 78 (see FIG. 13). The surgical drill 78 may be configured to rotate the guide pin 80 in order to drill the shallow dent 74 in the bone surface 76.

At block 112, the user may align a trajectory of the guide pin 80 to a virtual trajectory 82 that may be presented within the AR environment 48. The virtual trajectory 82 may be indicated by a dot or an axis that is presented within the AR environment 48 and is intended to provide a visual indication of the desired trajectory T of the guide pin 80.

Figure 14:
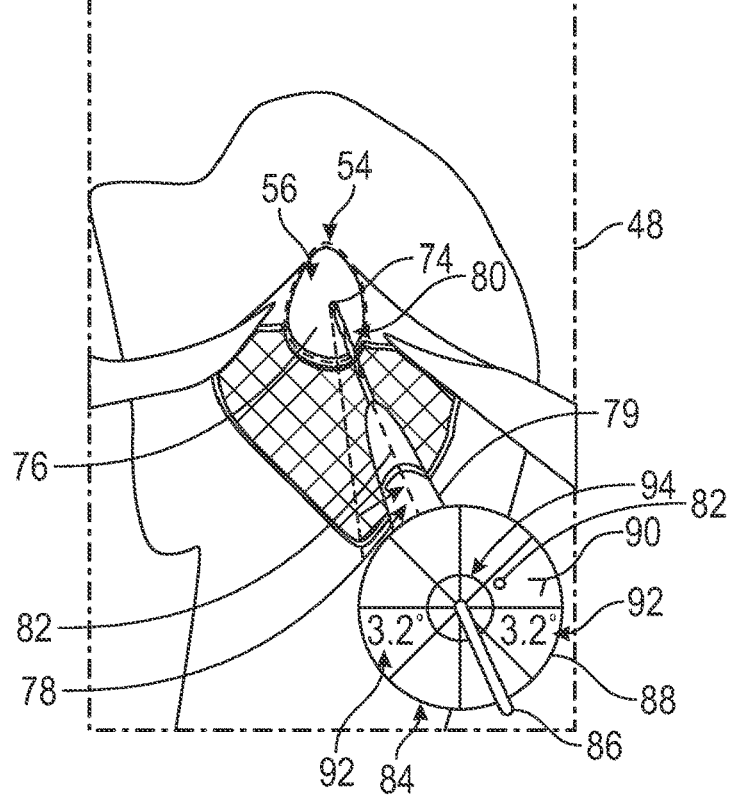
FIG. 14 illustrates additional aspects of a transfer module of an augmented reality environment.

The alignment step of block 112 of the method 100 is visually depicted in FIG. 14 and may be achieved by using a trajectory marker 84 that may be connected to the guide pin 80 for tracking a central axis of the guide pin 80. The trajectory marker 84 may be utilized to digitize the trajectory of the central axis of the guide pin 80, for example.

In an embodiment, the trajectory marker 84 includes a self-calibrated, slide-on disk design that includes an inner diameter that is slightly larger than the outer diameter of the guide pin 80. The trajectory marker 84 may be slid over a proximal portion 86 of the guide pin 80 that protrudes proximally from a rear surface 88 of the surgical drill 78. In an embodiment, the guide pin 80 extends entirely through a housing 79 of the surgical drill 78.

The user may align the trajectory of the guide pin 80 to the virtual trajectory 82 by pivoting the guide pin 80 about the pivot point established by the shallow dent 74. As the guide pin 80 is moved about the pivot point, various visual indicators may be presented to the user within the AR environment 48 for providing targeting guidance for aligning the trajectory of the guide pin 80 to the virtual trajectory 82. For example, a directional indicator 90 may be provided to visually depict the direction the user needs to pivot the guide pin 80 toward in order to move closer to the desired trajectory indicated by the virtual trajectory 82. An angular difference indicator 92 for indicting the angular difference between the actual trajectory of the guide pin 80 and the virtual trajectory 82 may further be provided as a visual reference within the AR environment 48.

In some implementations, an indicator ring 94 that overlays the trajectory marker 84 may be presented within the AR environment 48 (see, e.g., FIG. 14). The indicator ring 94 may be configured to automatically change from a first color (e.g., red or amber) to a second color (e.g., green) when the trajectory of the guide pin 80 is moved from an inadequate alignment position (e.g., greater than about 3 degrees of error) to an adequate alignment position (e.g., less than about 3 degrees of error) relative to the virtual trajectory 82.

After achieving the desired trajectory via the assistance provided by the trajectory marker 84, the guide pin 80 may be drilled into the anatomy 56 at block 114. Subsequent reaming processes may then be performed at block 116 for preparing the anatomy 56 for receiving a desired arthroplasty implant (e.g., a glenoid baseplate).

The exemplary surgical method 100 discussed above assumes the use of a guide pin for preparing a bone or joint for receiving an implant during an arthroplasty procedure. However, this disclosure is not limited to positioning guide pins and could extend to the positioning of any surgical positioning object that might be used to transfer aspects of a preoperative surgical plan to the intraoperative anatomy.

The exemplary surgical systems and methods of this disclosure advantageously provide improved intraoperative guidance for transferring preoperative surgical plans to the intraoperative anatomy during orthopedic surgical procedures. The intraoperative guidance may be presented within one or more augmented reality environments that may be overlayed onto the in-situ anatomy without occluding the user's view of the native anatomy. The improved guidance during transfer therefore provides improved surgical outcomes.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An augmented reality system for a surgical system, comprising:
an augmented reality visualization device; and
a processor programmed to control the augmented reality visualization device to:
provide an augmented reality environment relative to a patient's anatomy;
allow a user to interface with the augmented reality environment for intraoperatively achieving a desired entry point and a desired trajectory of a surgical positioning object relative to the patient's anatomy;
virtually indicate the desired trajectory within the augmented reality environment with a virtual trajectory indicator; and
virtually indicate a difference between the desired trajectory and an actual trajectory of the surgical positioning object within the augmented reality environment with a directional indicator or an angular difference indicator,
wherein the virtual trajectory indicator and at least one of the directional indicator or the angular difference indicator are overlaid onto a trajectory marker that is connected to the surgical positioning object, the trajectory marker being a physical object that is separate from the patient's anatomy.

2. The augmented reality system as recited in claim 1, wherein the processor is further programmed to control the augmented reality visualization device to virtually indicate the desired entry point with a virtual object.

3. The augmented reality system as recited in claim 2, wherein the virtual object includes a virtual crosshair.

4. The augmented reality system as recited in claim 1, wherein the processor is further programmed to control the augmented reality visualization device to visually indicate an accuracy between the actual trajectory and the desired trajectory of the surgical positioning object within the augmented reality environment.

5. The augmented reality system as recited in claim 4, wherein the processor is further programmed to control the augmented reality visualization device to visually indicate the accuracy by altering a color of a virtual indicator presented within the augmented reality environment.

6. The augmented reality system as recited in claim 1, wherein the surgical positioning object is a surgical guide pin.

7. The augmented reality system as recited in claim 1, wherein the trajectory marker includes a self-calibrated slide-on component that includes an inner diameter that is larger than an outer diameter of the surgical positioning object.

8. The augmented reality system as recited in claim 7, wherein the self-calibrated slide-on component is a disk.

9. The augmented reality system as recited in claim 1, wherein the directional indicator visually depicts a direction the surgical positioning object needs to move toward to achieve the desired trajectory.

10. The augmented reality system as recited in claim 1, wherein the trajectory marker is slidable along a portion of the surgical positioning object that protrudes rearwardly from a surgical drill.

11. The augmented reality system as recited in claim 10, wherein the surgical positioning object extends entirely through a housing of the surgical drill.

12. A surgical method, comprising:
intraoperatively demarcating a desired entry point and a desired trajectory of a surgical positioning object within an augmented reality environment produced by an augmented reality system, wherein both the desired entry point and the desired trajectory are derived from a preoperative surgical plan that is specific to a patient's anatomy; and
providing a visual indication of an accuracy between an actual trajectory and the desired trajectory of the surgical positioning object within the augmented reality environment,
wherein providing the visual indication includes virtually overlaying the visual indication of the accuracy onto a trajectory marker that is connected to the surgical positioning object, the trajectory marker being a physical object that is separate from the patient's anatomy.

13. The surgical method as recited in claim 12, wherein intraoperatively demarcating the desired entry point includes presenting a virtual crosshair within the augmented reality environment.

14. The surgical method as recited in claim 12, wherein intraoperatively demarcating the desired trajectory includes presenting a virtual trajectory within the augmented reality environment.

US 12,629,157 B2

15

15. The surgical method as recited in claim 12, wherein providing the visual indication of the accuracy includes presenting a directional indicator within the augmented reality environment.

16. The surgical method as recited in claim 12, wherein providing the visual indication of the accuracy includes presenting an angular difference indicator within the augmented reality environment.

17. The surgical method as recited in claim 12, wherein the trajectory marker is configured to digitize the actual trajectory of the surgical positioning object.

18. The surgical method as recited in claim 12, comprising, prior to intraoperatively demarcating the desired entry point and the desired trajectory, registering a virtual bone model to the patient's anatomy within the augmented reality environment.

19. The surgical method as recited in claim 12, wherein the surgical positioning object is a surgical guide pin.

20. A surgical method, comprising:

positioning a tip of a surgical guide pin at a location of a bone surface of an anatomy, wherein the location is indicated by a virtual crosshair within an augmented reality environment;

preparing an indentation at the location;

pivoting the surgical guide pin about a pivot point established by the indentation;

aligning an actual trajectory of the surgical guide pin to a virtual trajectory of the surgical guide pin within the augmented reality environment; and after preparing the indentation, pivoting the surgical guide pin, and aligning the actual trajectory to the virtual trajectory of the surgical guide pin, drilling the surgical guide pin into the anatomy.

21. The surgical method as recited in claim 20, wherein the pivot point is located on the bone surface.

22. An augmented reality system for a surgical system, comprising:

an augmented reality visualization device; and a processor programmed to control the augmented reality visualization device to:

provide an augmented reality environment relative to a patient's anatomy; and allow a user to interface with the augmented reality environment for intraoperatively achieving a desired entry point and a desired trajectory of a surgical positioning object relative to the patient's anatomy, wherein the processor is further programmed to control the augmented reality visualization device to perform a registration process without using fiducial markers for registering a virtual bone model to the patient's anatomy within the augmented reality environment, wherein the processor is further configured to control the augmented reality visualization device to present a plurality of registration reference points within the augmented reality environment, and further wherein each of the plurality of registration reference points visually indicates a location where the user should physically touch the patient's anatomy in order to initialize an approximation of the virtual bone model to the patient's anatomy.

* * * * *